(12) United States Patent
Pecheur et al.

(10) Patent No.: US 9,234,848 B2
(45) Date of Patent: Jan. 12, 2016

(54) COMPOUNDS HAVING CHROMOPHORE AND PHOTOREACTIVE GROUPS

(75) Inventors: Eve-Isabelle Pecheur, Lyons (FR); Line Bourel-Bonnet, Geispolsheim (FR); Benoit Hilbold, Strasbourg (FR)

(73) Assignees: CENTRE NATIONAL DE LA RECHERCHE SCIENTIFIQUE (C.N.R.S.), Paris (FR); UNIVERSITE CLAUDE BERNARD LYON 1, Villeurbanne (FR); UNIVERSITE DE STRASBOURG, Strasbourg (FR)

( * ) Notice: Subject to any disclaimer, the term of this patent is extended or adjusted under 35 U.S.C. 154(b) by 0 days.

(21) Appl. No.: 14/007,480

(22) PCT Filed: Mar. 23, 2012

(86) PCT No.: PCT/EP2012/055159
§ 371 (c)(1),
(2), (4) Date: Oct. 23, 2013

(87) PCT Pub. No.: WO2012/130740
PCT Pub. Date: Oct. 4, 2012

(65) Prior Publication Data
US 2014/0045173 A1  Feb. 13, 2014

(30) Foreign Application Priority Data

Mar. 25, 2011 (FR) ..................... 11 52498

(51) Int. Cl.
| | | |
|---|---|---|
| *A61K 9/00* | (2006.01) | |
| *G01N 21/64* | (2006.01) | |
| *C09B 11/24* | (2006.01) | |
| *G01N 33/58* | (2006.01) | |
| *C07D 493/10* | (2006.01) | |
| *C07C 59/84* | (2006.01) | |
| *C07C 237/22* | (2006.01) | |

(52) U.S. Cl.
CPC ............ *G01N 21/6486* (2013.01); *C07C 59/84* (2013.01); *C07C 237/22* (2013.01); *C07D 493/10* (2013.01); *C09B 11/24* (2013.01); *G01N 33/582* (2013.01)

(58) Field of Classification Search
CPC ................................... A61K 41/0042
See application file for complete search history.

(56) References Cited

U.S. PATENT DOCUMENTS

2009/0305410 A1 12/2009 Mao et al.
2010/0009353 A1 1/2010 Barnes et al.

FOREIGN PATENT DOCUMENTS

CN 101 967 207 A 2/2011

OTHER PUBLICATIONS

Speers A E et al.: "Profiling Enzyme Activities in Vivo Using Click Chemistry Methods", Chemistry and Biology. Current Biology, London. GB. vol. 11. No. 4. Apr. 1, 2004, pp. 535-546, XP025916602, ISSN: 1074-5521. DOI: 10.1016/J.CHEMBIOL.2004.03.012, [retrieved on Apr. 13, 2004], p. 535, paragraph summary p. 537; compound 7, p. 544. paragraph 4, the whole document, Cited in French Search Report and ISR.

Andrew L. Mackinnon et al.: "Photo-Leucine Incorporation Reveals the Target of a Cyclodepsipeptide Inhibitor of Cotranslational Translocation", Journal of the American Chemical Society, vol. 129, No. 47, Nov. 1, 2007, pp. 14560-14561, XP055016377, ISSN: 0002-7863, DOI: 10.1021/ja076250y p. 14560; figure 1, Cited in French Search Report and ISR.

International Search Report, dated Jun. 1, 2012, from corresponding PCT application.

French Search Report, dated Jan. 24, 2012, from corresponding French application.

*Primary Examiner* — Paul Dickinson
(74) *Attorney, Agent, or Firm* — Young & Thompson

(57) ABSTRACT

The invention relates to the field of hydrophobic photoaffinity marking by element of probes that are multifunctional lipid compounds. The compounds include at least one chromophore group and two lipid chains, one of which includes a photoreactive group. The compounds can be used for the study and identification of hydrophobic regions or domains within proteins, particularly within viruses.

29 Claims, No Drawings

COMPOUNDS HAVING CHROMOPHORE AND PHOTOREACTIVE GROUPS

The invention relates to the field of hydrophobic photoaffinity marking by means of probes which are multi-functional lipid compounds. These compounds comprise at least one chromophore group and two lipid chains, one of which comprises a photoreactive group. These compounds may be used for studying and identifying hydrophobic areas or domains within proteins, notably within viruses.

Probes which allow marking or identification of hydrophobic domains within proteins are known. However, the probes from the state of the art use detection by means of a radioactive element such as $^{125}I$ which emits gamma radiations. In addition to the difficulties encountered during their preparation, such probes also have risks during their use. Thus, the use of such probes is limited or even prevented for certain applications.

As an example of probes for identifying hydrophobic protein domains, the ones described by Brunner are known, which apply $^{125}I$ with the drawbacks and problems which result from this (Annu. Rev. Biochim. 1993. 62. 483-514).

Moreover, the use of trifunctional probes is known for identifying enzymes (Speers et al., "Profiling enzyme activities in vivo using click chemistry method" published on Apr. 1, 2004). However, the probes used do not have any photoreactive properties.

From US-2009/305410, the identification of polypeptides or proteins is also known by means of different fluorescent compounds comprising water-soluble polymeric fragments.

Therefore, there exists a need for having probes for marking or identifying proteins which provide a solution to these problems and which give the possibility of avoiding the drawbacks related to the use of the known probes.

The present invention gives the possibility of providing a solution to all or part of the problems related to the probes of the state of the art.

Thus, and in a particularly advantageous way, the invention provides compounds which meet at least two distinct criteria: they are photoreactive and they are detectable for example by fluorescence. Still more advantageously, these compounds according to the invention have at least three functionalities. They have a lipid structure, and they may be activated photochemically and are detectable. These three functionalities are connected together through a common platform.

Thus, the present invention provides a probe in the form of a compound comprising an at least trifunctional binding platform, substituted with
- at least one chromophore group selected from an absorbing group, a fluorescent group or a luminescent group;
- a first hydrocarbon chain functionalized at one end bound to the platform;
- a second hydrocarbon chain, comprising a photoreactive group and functionalized at an end bound to the platform.

Advantageously, the compound according to the invention is of formula (I) and comprises:
- an at least functional binding platform Q, substituted with at least one chromophore group $Q^1$ selected from an absorbing group, a fluorescent group or a luminescent group;
- a first hydrocarbon chain bound to Q via a functional group $L^1$;
- a second hydrocarbon chain bound to Q via a functional group $L^2$ and comprising a photoreactive group $Q^2$;

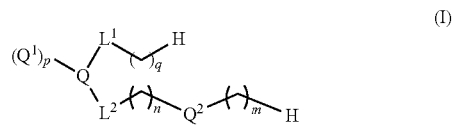

(I)

wherein
- Q represents an at least trifunctional binding platform;
- p represents 1, 2 or 3;
- $Q^1$, either identical or different, independently represents a chromophore group selected from an absorbing group, a fluorescent group or a luminescent group;
- $L^1$ and $L^2$, either identical or different, represent independently a group selected from NH, C(O), S, O;
- $Q^2$ represents a photoreactive group;
- m represents an integer ranging from 0 to 24;
- n represents an integer ranging from 1 to 24;
- the sum of m and of n is comprised between 1 and 30;
- q represents an integer ranging from 1 to 30.

Preferably, the compound according to the invention is a compound of formula (I) wherein
- p represents 1 and $Q^1$ represents a fluorescent group; or
- p represents 2 and $Q^1$ independently represents two fluorescent groups, either identical or different; a fluorescent group and an absorbing group; a fluorescent group and a luminescent group; or
- p represents 3 and $Q^1$ independently represent a luminescent group and two fluorescent groups either identical or different.

Preferably for the compound according to the invention, the at least trifunctional binding platform or Q represents a group selected from amino acid derivatives, glycerol derivatives, carboxylic triacid derivatives, triamine derivatives; in particular a group derived from an alpha-amino acid and comprising two amine functions and a carbonyl function. Thus, the invention also relates to a compound of formula (II)

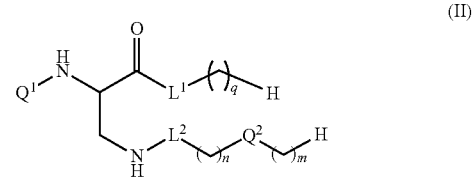

(II)

wherein $Q^1$, $L^1$, $L^2$, $Q^2$, m, n and q are as defined for the compound of formula (I). Advantageously, the invention also relates to a compound of formula (III)

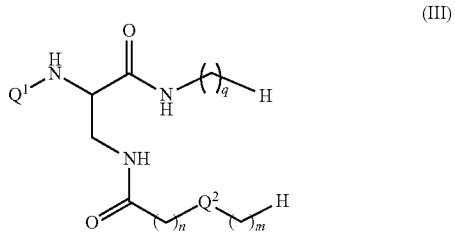

(III)

wherein $Q^1$, $Q^2$, m, n and q are as defined for the compounds of formula (I) or formula (II).

Preferably, the invention relates to a compound of formula (I), (II) or (III) wherein m represents an integer ranging from 1 to 12; or
n represents an integer ranging from 1 to 12; or
q represents an integer ranging from 6 to 26; or
the sum of m and of n is comprised between 4 and 24;
or a compound of formula (I), (II) or (III) wherein
m represents an integer ranging from 1 to 12; and
n represents an integer ranging from 1 to 12; and
q represents an integer ranging from 8 to 24; and
the sum of m and of n is comprised between 6 and 18.

Advantageously for the compound according to the invention, the chromophore group or $Q^1$ is independently selected from rhodamine, fluorescein, rhodamine derivatives, substituted rhodamine and fluorescein derivatives. Substituted fluorescein, notably such as the fluorophores commercially available from Molecular Probes (Invitrogen) and covering a wide fluorescence range, coloring agents, colored substances with absorption in the visible range (400 to 800 nm) luciferin, luminol, luminol derivatives.

Preferably, the chromophore group or $Q^1$ is selected from rhodamine and its analogs, for example carboxytetramethylrhodamine.

Also advantageously, the compound according to the invention may comprise two chromophore groups, for example a rhodamine derivative and a fluorescein derivative. The presence of two chromophore groups within the compound according to the invention is particularly advantageous when it is applied for uses according to the fluorescence resonance energy transfer principle (FRET).

Advantageously for the compound according to the invention, the photoreactive group or $Q^2$ is independently selected from carbene generating groups, nitrene generating groups, arylketone derivatives.

Preferably, the photoreactive group or $Q^2$ is independently selected from a group comprising a diazo or diazoester function, a group derived from diazirine, notably 3-trifluoromethyl-3-phenyl-diazirine (TID) or pentafluorophenylazide, a group comprising an arylazide, acylazide, alkylazide, diazoester function, a group derived from benzophenone and a group of formula (IV)

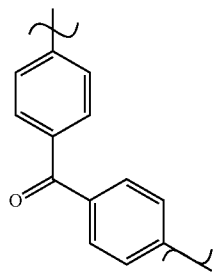

(IV)

In a particularly advantageous way, the compound according to the invention is hydrophobic so that it has particular affinity for hydrophobic areas of substrates with which it may be put into contact.

In addition to a compound useful as a probe, the invention also relates to a method for preparing such a compound. This preparation method according to the invention comprises the reaction of a compound comprising an at least trifunctional binding platform;

of at least one compound comprising a chromophore group selected from an absorbing group, a fluorescent group and a luminescent group;

of a compound comprising a first hydrocarbon chain functionalized at one end;

of a compound comprising a second hydrocarbon chain functionalized at one end and comprising a photoreactive group.

Generally, for the preparation method according to the invention, the order of the steps is not essential. Thus, the order of application of the different reagents is indifferent, this order may easily be adapted according to the reagents used or further according to the reaction conditions.

The preparation method according to the invention gives the possibility of preparing the whole of the compounds according to the invention, in particular the compounds of formulae (I), (II) or (III) as well as their preferred analogs.

Advantageously, the method according to the invention applies an at least trifunctional binding platform which comprises a free primary amine function, a protected primary amine function and a carboxylic acid function.

Advantageously, the method according to the invention then comprises the steps:

of reacting the primary amine function with the compound comprising a first hydrocarbon chain, functionalized at one end;

of reacting the carboxylic acid function with the compound comprising a second hydrocarbon chain, functionalized at one end and comprising a photoreactive group;

of deprotecting the protected primary amine function;

of reacting the deprotected primary amine function with the compound comprising a chromophore group selected from an absorbing group, a fluorescent group or a luminescent group.

The method according to the invention may be applied for preparing a compound according to the invention, in particular for preparing a compound of formula (I), of formula (II) or of formula (III).

In a particular way, the preparation method according to the invention applies, as a platform, a commercially available α-aminoacid backbone: Nα-Boc-L-2,3-diaminopropionic acid (Boc-Dpr-OH). It has the advantage of having three different functionalities: a free primary amine, a protected primary amine and a free carboxylic acid and is capable of selectively and successively reacting by forming a peptide bond with three different molecules.

Benzophenone is selected as a photoreactive group and is integrated within a fatty acid. Finally, a rhodamine derivative is used as a chromophore group:carboxytetramethylrhodamine (CTMR). This derivative has advantageous properties such as its fluorescence as well as its stability under synthesis conditions and its relative insensitivity to pH modifications.

The preparation method according to the invention may be applied according to the chaining sequence of schemes 1, 2 and 3.

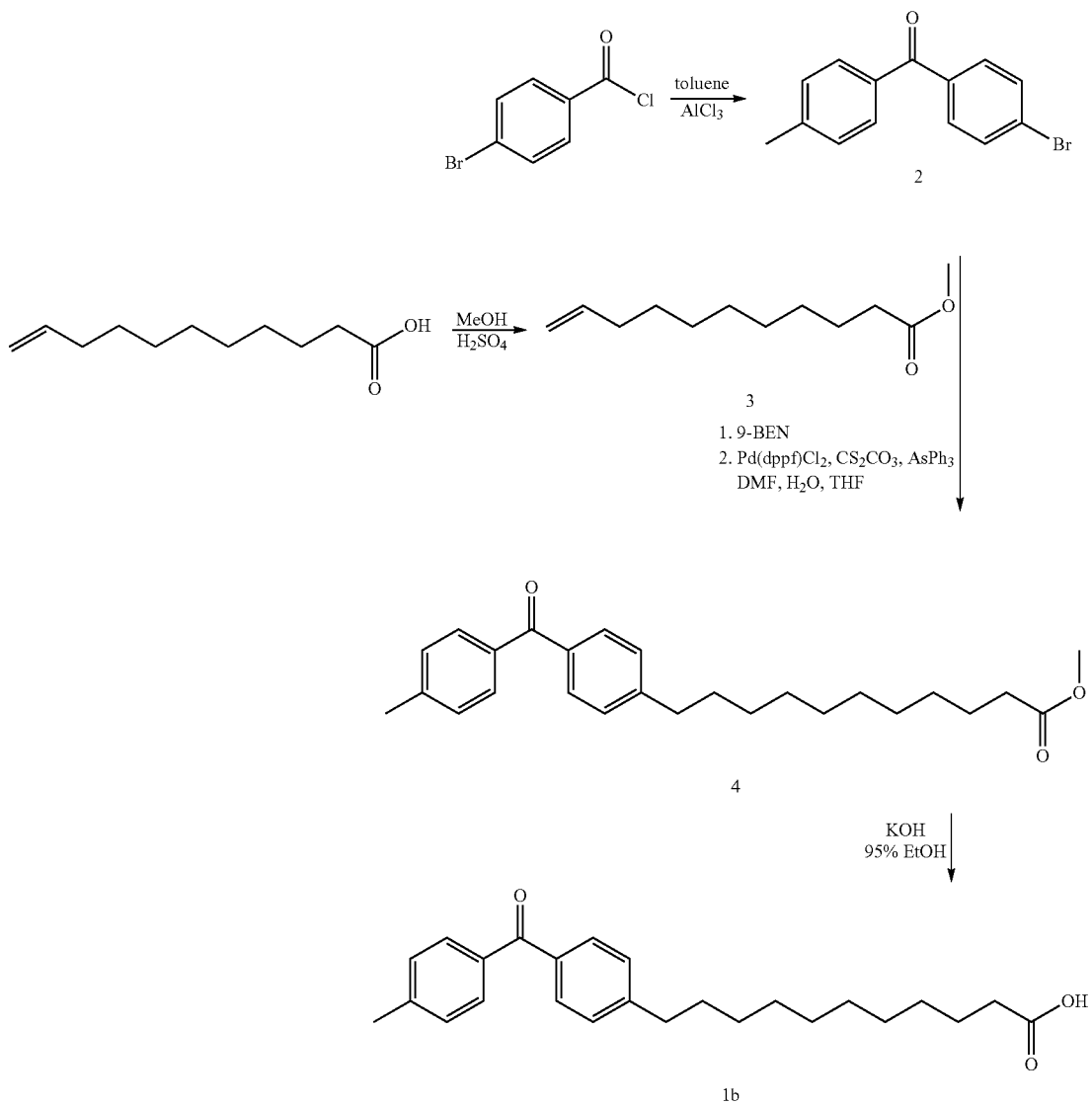

Thus, three lipid precursors 1a-c are prepared according to a well-known procedure or else according to the preparation method according to the invention. Thus, the compounds 1a and 1b may be prepared according to the method described by Lala et al. (*J. Am. Chem. Soc.* 1993, 115, 3982-3988) and by Gan et al. (*J. Org. Chem.*, 2006, 71, 9487-9490); while the lipid precursor 1c may be prepared from the method described by Gan et. al. (J. Org. Chem., 2006, 71, 9487-9490) modified according to the conditions of Scheme 2.

Scheme 2

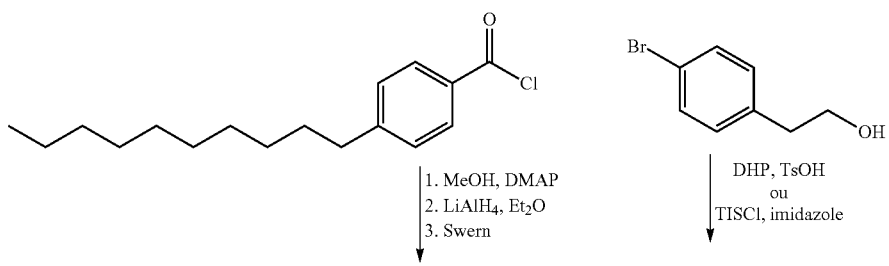

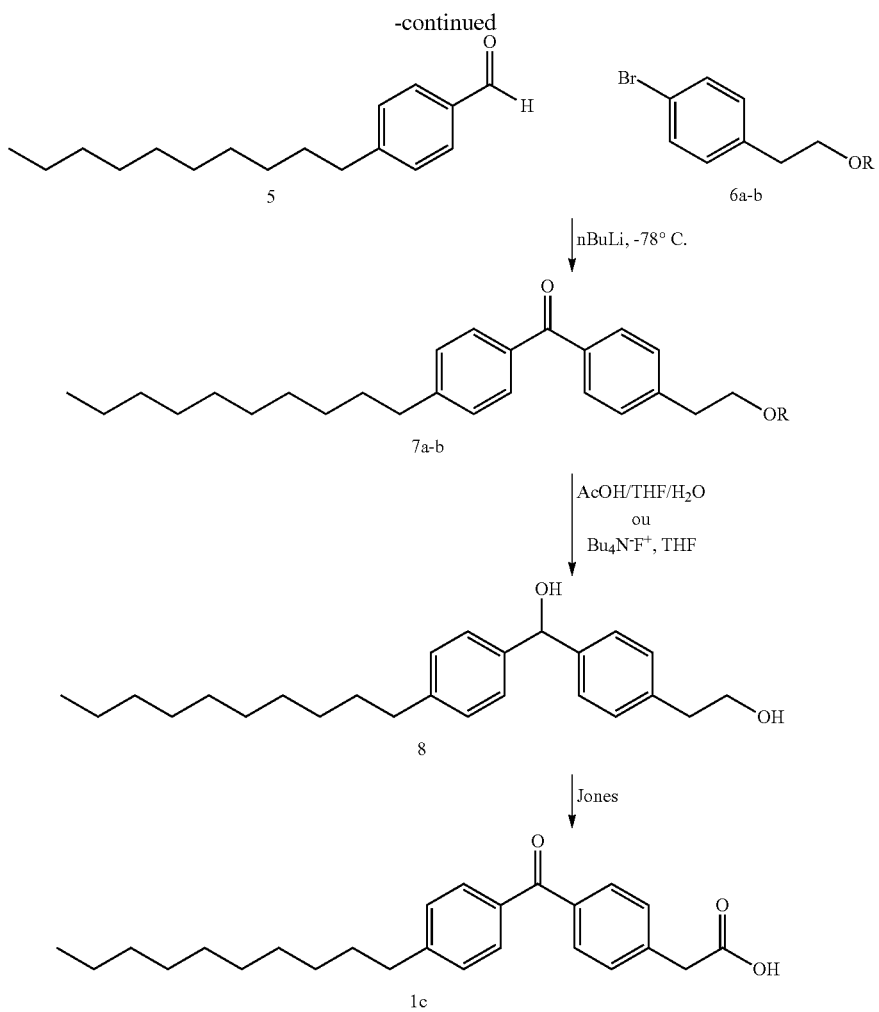

The precursor, 4-n-decylbenzaldehyde, 5, may be prepared in three steps with a good yield (77%) from commercially available 4-decylbenzoyl chloride. First of all, the acyl chloride is transformed into its methyl ester and then completely reduced into its corresponding alcohol. The primary alcohol is oxidized in 5 by using the method described by Omura and Swern (Tetrahedron 1978, 34, 1651-1660). Alternatively, the precursor 5 may also be synthesized in a single step by a Rosemund reduction from 4-decylbenzoyl chloride with a yield of 64%. In parallel, two strategies are available for protecting the commercially available alcohol, 2-(4-bromophenyl)ethanol. First of all, dihydropyrane (DHP) is used and after 6 hours of reaction, the corresponding acetal 6a is obtained with a yield of 92% and then coupled with the aldehyde 5 with a yield of 19%. An alternative strategy consists of using triisopropylsilyl chloride (TIPSCI) in the presence of imidazole for allowing conversion of 2-4-bromophenyl into its corresponding silyl ether 6b with a very high yield (99%) and within 2 hours. The compound 6b is treated with n-butyl-lithium at −78° C. and then coupled with 5 in order to obtain the secondary alcohol 7b in the form of a colorless oil with a yield of 70%. Next, tetra-n-butylammonium fluoride (TBAF) is used for deprotecting 7b and the primary alcohol 8 is obtained with a yield of 73%. Finally, 8 is oxidized twice according to the Jones method in order to obtain 1c in the form of white solid with a yield of 91%.

Starting from 4-n-decylbenzaldehyde, the global yield of the synthesis is 46% while it is only 22% with the synthesis methods already described in the literature. Finally, the overall yield of this synthesis is 35%, 7 steps may be required for obtaining the final product 1c from the commercially available 4-decylbenzoyl chloride according to a convergent synthesis strategy. Thus, it is possible to obtain (4-(4-decylbenzoyl)phenyl)ethanoic acid ($C_{10}$—BP—$C_1$—COOH, 1c) with a good yield and a reduced number of steps, from the aldehyde.

This improvement opens a more effective route for the synthesis of other analogs according to the preparation method according to the invention.

The lipid precursors 1a-c may be used for preparing the compounds 12a-c according to the invention according to Scheme 3.

Scheme 3

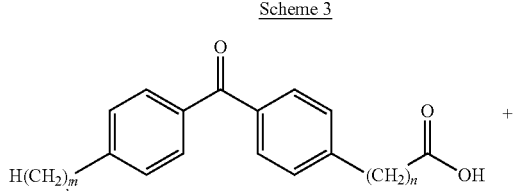

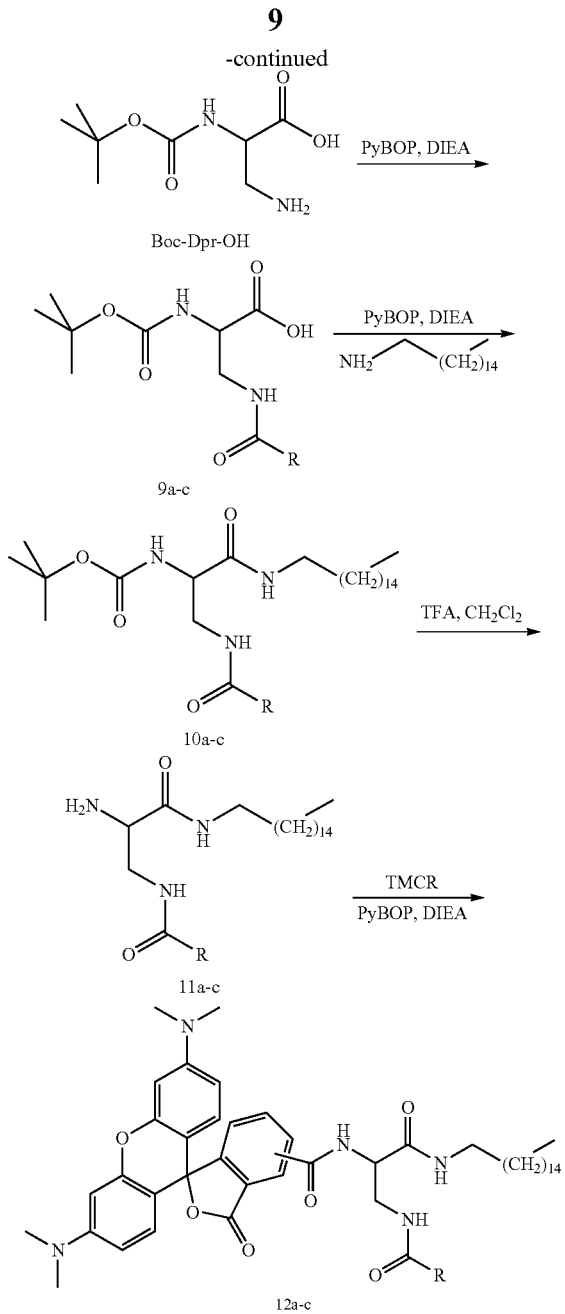

Three lipid precursors or analogs of a fatty acid comprising a benzophenone group (FABP) 1a-c are thus available and used in the synthesis of compounds according to the invention, notably useful as new lipid probes.

All the experiments are conducted away from light. In order to check the state of progress of each state of the synthesis with UVs, the fatty acid containing the benzophenone (FABP) is introduced onto the backbone or platform during the first step for synthesis of the compounds according to the invention. To do this, the carboxylic acid function of this synthon is activated by means of PyBOP in a basic medium (DIEA). Then, Boc-Dpr-OH is added to the solution. After treatment, Boc-Dpr(FABP)-OH compounds 9a-c are isolated, characterized and then the free carboxylic acid function of Boc-Dpr(FABP)-OH is activated with PyBOP in the presence of DIEA before adding hexadecylamine. Boc-Dpr(FABP)-NH—$C_{16}H_{33}$ compounds 10a-c are isolated, characterized and the amine function is then deprotected in an acid medium: a mixture of TFA and of dichloromethane (1/1 v/v). After treatment, H-Dpr(FABP)-NH—$C_{16}H_{33}$ compounds 11a-c are isolated and characterized. Finally and very advantageously, CTMR is the last synthon to be introduced on the backbone. After activating the carboxylic acid function of CTMR with PyBOP in the presence of DIEA, H-Dpr(FABP)-NH—$C_{16}H_{33}$ is added. The progression of the reaction is followed by TLC. After treatment, the Rhod-Dpr(FABP)-NH—$C_{16}H_{33}$ compounds 12a-c are isolated in the form of a purple powder. All the final or intermediate compounds are characterized by TLC, MS or NMR. It should be noted that carboxytetramethylrhodamine is commercially available, in particular in the form of a mixture of two regioisomers. These two regioisomers are detectable by HPLC but are generally separable with difficulty. This separation is not required for the use of the compounds according to the invention, in particular as probes in a biological medium.

According to another aspect, the invention relates to the use of a compound according to the invention for identifying a protein.

Thus, the invention relates to a method for identifying a protein comprising the use of a compound according to the invention, preferably the use of a hydrophobic compound according to the invention.

Thus and advantageously, the identification method according to the invention is applied for identifying a hydrophobic fragment within a protein.

Also advantageously, the identification method according to the invention is applied for identifying one or several transmembrane domains within a membrane protein.

Preferably, the identification method according to the invention is applied for identifying a fusion protein or a viral fusion peptide. The fusion protein to be identified may be a fusion protein of a hepatitis virus, for example hepatitis B or hepatitis C, or further of HIV, an influenza virus or a veterinary virus.

Also preferably, the identification method according to the invention comprises
  a—putting the compound into contact with the protein;
  b—photoactivating the compound or the photoreactive group of the compound;
  c—reacting the photoactivated group of the compound with the protein;
  d—activating and detecting or detecting the fluorescence or the absorbance of the chromophore group within the reaction product.

Advantageously, the putting of the compound according to the invention into contact with the protein is carried out by means of micelles or systems with lipid bilayers, for example liposomes.

The identification method according to the invention comprises the photoactivation of a compound according to the invention which is advantageously carried out
  with a source selected from a lamp or a laser; or
  the activation power is comprised from 0.1 and 1,000 W; or
  the wavelength is comprised between 250 and 500 nm; or
  the activation time is comprised between 1 second and 2 hours, regardless of whether this is carried out continuously or in a sequenced or pulsed way.

In a particularly advantageous way, the identification method according to the invention allows a very wide identification range by means of the hydrophobic photomarking of many protein domains or areas. Indeed, depending on the position of the photoactivatable group on the lipid chain within the compound according to the invention which is used, this compound will be able to particularly bind and in a specific position within the protein to be identified. In the same way, the other lipid chain, notably because of its length, may be adapted depending on the encountered lipid or membrane environment when applying the identification method according to the invention. Thus, the adaptation of the length of the lipid chains allows the compound according to the invention to be suitably positioned within the hydrophobic domain of the protein, notably by avoiding or limiting its movements or by limiting or avoiding that its lipid chains fold back on themselves thereby preventing their proper positioning towards the studied hydrophobic domain or the one to be identified.

The compound according to the invention applied for the identification method according to the invention therefore allows suitable anchoring within the protein to be identified.

Moreover, among all the photoreactive or photoactivatable chemical groups which may be present within the compound according to the invention, the benzophenone is particularly advantageous for studying protein-protein and protein-lipid interactions. Indeed, since the activation wavelength of benzophenone is located around 365 nm, degradation of the proteins is limited or even nil, therefore giving the possibility of conducting studies in a cell medium or within other living systems.

Further, the radical generated during the benzophenone photoactivation will react in the hydrophobic medium on a C—H bond covalently with a good yield and therefore allows specific identification of the chemical environment of the adduct formed.

Finally, the benzophenone is chemically stable towards ambient light and towards most synthesis conditions used in chemistry.

The different aspects of the invention may be illustrated by the following examples.

PREPARATION METHOD AND COMPOUND EXAMPLES

The amino acid Boc-L-Dpr-OH is purchased from Iris Biotech GmbH. Ninhydrin, phosphomolybdic acid and trifluoroacetic acid come from Sigma-Aldrich. Carboxytetramethylrhodamine and PyBOP are purchased from Novabiochem. The hexadecylamine comes from Aldrich and the DIEA from Alfa Aesar. 6-(4-(4-n-hexylbenzoyl)phenyl)hexanoic acid is synthesized according to the procedure mentioned above. The chemical reagents are used without any additional purification. $CH_2Cl_2$ and THF are distilled under an inert atmosphere (argon flow) and dried on $CaH_2$ and sodium (in the presence of benzophenone) respectively. Chromatography is carried out on silica gel 60 (40-63 µm): the powder and the aluminum plates for the TLCs are purchased from Merck. The $^1H$ and $^{13}C$ NMR spectra are recorded on 300 MHz or 400 MHz Brucker apparatuses. The chemical shifts of the proton (a) are reported in ppm and the spectrum is calibrated relatively to the peak of the deuterated residual solvents. The coupling constants (J) are reported in Hz. The mass spectra (ES-MS) are recorded on a Mariner ESI/TOF mass spectrometer. For the compounds described for the first time, high resolution mass (HR-MS) is measured on a mass GC/TOF spectrometer from Agilent. The melting points are measured on a Buchi B-540. The HPLC analyses are carried out with a Jupiter 5u $C_4$ 300 Å column (150×4.6 mm, C4) from Phenomenex with a flow rate of 1 mL/min by using a linear gradient of 10 min from 0 to 100% of $CH_3CN$ in water (0.1% of TFA), followed by 5 mins at 100% $CH_3CN$ (0.1% of TFA). The retention times (Rt) of the HPLC analysis are shown in minutes.

(4-(4-decylbenzoyl)phenyl)ethanoic acid
Methyl 4-decylbenzoate
$C_{18}H_{28}O_2$—MW: 276.4 g·mol$^{-1}$

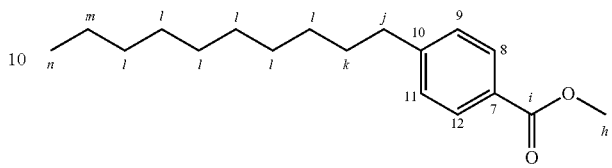

4-decylbenzoyl chloride (1.00 g-3.56 mmol) is dissolved in 10 mL of methanol with stirring and at room temperature. Next, dimethylaminopyridine (43 mg-0.36 mmol) is added to the solution and the reaction medium is left with stirring for 1 hour. The methanol is then evaporated under reduced pressure and the solution is then re-dissolved in 20 mL of $CH_2Cl_2$. The resulting mixture is washed with water (2×20 mL). The aqueous phase is extracted with $CH_2Cl_2$ and the recovered organic phases are dried on $MgSO_4$, filtered and the solvent is evaporated under reduced pressure. The product formed is dried under a vane pump overnight in order to lead to the desired product in the form of a colorless oil (973 mg—Yield: 99%).

TLC: Rf=0.7 (cyclohexane/AcOEt 8/2 v/v)

$^1H$ NMR (400 MHz; CDCl$_3$) δ=7.96 (d, 2H$_{8+12}$, J=8.2), 7.24 (d, 2H$_{9+11}$, J=8.2), 3.90 (s, 3H$_h$), 2.66 (t, 2H$_j$, J=7.8), 1.63 (m, 2H$_k$), 1.32-1.27 (m, 14H$_{l+m}$), 0.89 (t, 3H$_n$, J=6.7)

$^{13}C$ NMR (50 MHz; CDCl$_3$) δ=167.8 (C$_i$), 149.1 (C$_{10}$), 130.3 (C$_{8+12}$), 129.0 (C$_{9+11}$), 128.3 (C$_7$), 52.5 (C$_h$), 36.7 (C$_j$), 32.6, 31.8, 30.2, 30.2, 30.1, 30.0, 29.9 (C$_{i+k}$ for the seven peaks), 23.3 (C$_m$), 14.7 (C$_n$)

Mass: m/z=277.2 [M+H]$^+$, calculated mass=276.2

4-decylphenylmethanol
$C_{17}H_{28}O$—MW: 248.4 g·mol$^{-1}$

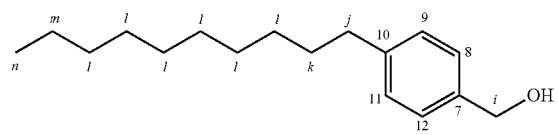

Lithium aluminum hydride (40 mg-1.03 mmol) is dissolved in 15 mL of diethyl ether with stirring, under argon and at room temperature in a dry flask provided with a condenser. Then, methyl 4-decylbenzoate (950 mg-3.43 mmol) is added dropwise to the solution and the reaction medium is left under stirring for 1 hour. 20 mL of water are then added with precaution to the solution and the latter is poured into iced water and a 10% $H_2SO_4$ (v/v) aqueous solution is then added. The aqueous phase is extracted with diethyl ether and the recovered organic phases are dried on $MgSO_4$, filtered and the solvent is evaporated under reduced pressure. The resulting residue is purified on a silica column (elution gradient cyclohexane/AcOEt 95/5 to 80/20 v/v) in order to lead to the desired product obtained in the form of white solid (768 mg—Yield: 90%).

TLC: Rf=0.6 (cyclohexane/AcOEt 8/2 v/v)

$^1H$ NMR (300 MHz; CDCl$_3$) δ=7.29 (d, 2H$_{8+12}$, J=7.9), 7.19 (d, 2H$_{9+11}$, J=7.9), 4.65 (s, 2H$_i$), 2.63 (t, 2H$_j$, J=7.8), 1.63 (m, 2H$_k$), 1.29 (m, 14H$_{l+m}$), 0.91 (t, 3H$_n$, J=6.8)

$^{13}$C NMR (50 MHz; CDCl$_3$) δ=143.1 (C$_7$), 138.8 (C$_{10}$), 129.2 (C$_{9+11}$), 127.8 (C$_{8+12}$), 65.9 (C$_i$), 36.3 (C$_j$), 32.6, 32.2, 30.3, 30.2, 30.0 (C$_{i+k}$ for the 5 peaks), 23.3 (C$_m$), 14.7 (C$_n$)

Mass (GCMS): m/z=246.2 [M]$^+$, calculated mass=248.2 g·mol$^{-1}$ 4-decylbenzaldehyde (5)

C$_{17}$H$_{26}$O—MW: 246.4 g·mol$^{-1}$

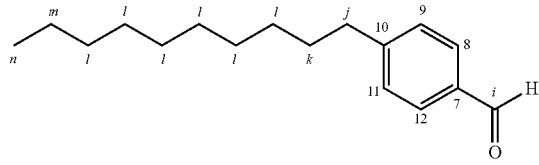 [SMILES: CCCCCCCCCCc1ccc(C=O)cc1]

To oxalyl chloride (390 μL-4.63 mmol) at −78° C., is added with precaution dimethylsulfoxide (460 μL-6.49 mmol) in solution in 10 mL of CH$_2$Cl$_2$ at −78° C., under argon and with stirring for 10 mins. Next 4-decylphenyl methanol (768 mg-3.09 mmol) dissolved in 10 mL of CH$_2$Cl$_2$ is carefully added at −78° C. The resulting solution is stirred for 20 mins. Triethylamine (1.73 mL-12.4 mmol) is then added and the solution is then left to return to room temperature. 20 mL of a saturated NaHCO$_3$ solution are then added to the reaction medium. The aqueous phase is extracted with diethyl ether (1×50 mL). The collected organic phases are washed with a saturated KHSO$_4$ solution, with a saturated NaHCO$_3$ solution and with brine and then dried on MgSO$_4$, filtered and the solvent is evaporated under reduced pressure in order to lead to the product 5 obtained in the form of a colorless oil (662 mg—Yield: 87%).

TLC: Rf=0.7 (cyclohexane/AcOEt 8/2 v/v)

$^1$H NMR (300 MHz; CDCl$_3$) δ=9.98 (s, 1H$_i$), 7.80 (d, 2H$_{8+12}$, J=8.0), 7.34 (d, 2H$_{9+11}$, J=8.1), 2.69 (t, 2H$_j$, J=7.8), 1.65 (m, 2H$_k$), 1.27 (m, 14H$_{l+m}$), 0.89 (t, 3H$_n$, J=6.6)

$^{13}$C NMR (50 MHz; CDCl$_3$) δ=192.5 (C$_i$), 151.1 (C$_{10}$), 135.1 (C$_7$), 130.5 (C$_{8+12}$), 129.7 (C$_{9+11}$), 36.9 (C$_j$), 32.6, 31.7, 30.2, 30.1, 30.0 (C$_{i+k}$ for the 5 peaks), 23.3 (C$_m$), 14.7 (C$_n$)

Mass: m/z=247.2 [M+H]$^+$, calculated mass=246.2 g·mol$^{-1}$ 4-bromophenethoxytriisopropylsilane (6b)

C$_{17}$H$_{29}$OBrSi—MW: 357.4 g·mol$^{-1}$

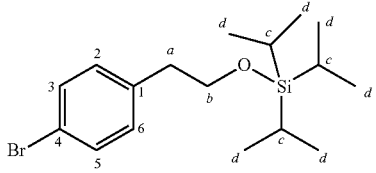

4-bromophenethyl alcohol (500 mg-2.48 mmol) is added to 10 mL of CH$_2$Cl$_2$ and then triisopropylsilyl chloride (720 mg-3.73 mmol) and imidazole (506 mg-7.44 mmol) are added thereto. The solution is stirred at room temperature for 2 hours. The organic phase is washed with a saturated NaHCO$_3$ solution (2×10 mL), with water (1×10 mL) and with brine (1×10 mL). The aqueous phase is extracted with CH$_2$Cl$_2$ (2×30 mL). The two collected organic phases are dried on MgSO$_4$, filtered and the solvent is then evaporated under reduced pressure. The resulting residue is purified on a silica column (elution gradient cyclohexane/AcOEt 100/0 to 100/10 v/v) in order to lead to the product 6b obtained in the form of a colorless oil (880 mg—Yield: 99%).

TLC: Rf=0.9 (cyclohexane/AcOEt 8/2 v/v)

$^1$H NMR (300 MHz; CDCl$_3$) δ=7.40 (m, 2H$_{3+5}$), 7.11 (m, 2H$_{2+6}$), 3.87 (t, 1H$_b$, J=6.9), 2.81 (t, 1H$_a$, J=6.9), 1.05 (m, 21H$_{c+d}$)

$^{13}$C NMR (CDCl$_3$) δ=139.0 (C$_1$), 131.9 (C$_{3+5}$), 131.6 (C$_{2+6}$), 120.6 (C$_4$), 65.1 (C$_b$), 39.8 (C$_a$), 18.6 (C$_d$), 12.7 (C$_c$)

Mass: m/z=357.1 [M+H]$^+$, calculated mass=356.1 g·mol$^{-1}$

Synthesis of (4-decylphenyl)(4-(2-(triisopropylsilyloxy)ethyl)phenyl)methanol (7b)

C$_{34}$H$_{56}$O$_2$Si—MW: 524.9 g·mol$^{-1}$

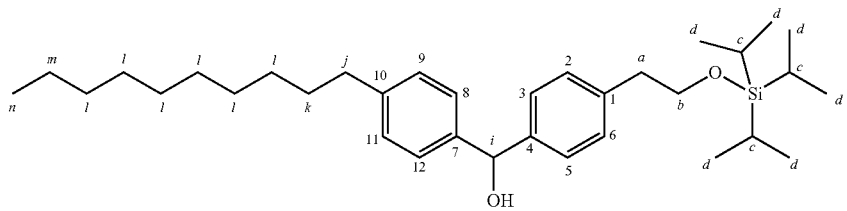 [SMILES: CCCCCCCCCCc1ccc(C(O)c2ccc(CCO[Si](C(C)C)(C(C)C)C(C)C)cc2)cc1]

The protected alcohol 6b (957 mg-2.67 mmol) is dissolved in 10 mL of THF with stirring, under argon and at −78° C. in a dry 2-neck flask. Then, n-butyl lithium (1.8 mL-2.92 mmol) is added dropwise to the solution and the latter is left under stirring at −78° C. for 1 hour. The aldehyde 5 (600 mg-2.43 mmol) dissolved in 10 mL of THF is then added dropwise, to the solution kept at −78° C. and the reaction medium is then left to return to room temperature and the solution is stirred for 12 hours. 20 mL of a saturated NaHCO$_3$ solution are added to the solution and the latter is then extracted with AcOEt. The recovered organic phases are washed with a solution of saturated NaHCO$_3$ and with brine and then dried on MgSO$_4$, filtered and the solvent is evaporated under reduced pressure. The resulting residue is purified on a silica column (elution gradient cyclohexane/AcOEt 100/0 to 100/7 v/v) in order to lead the product 7b obtained in the form of a colorless oil (892 mg—Yield: 70%)

TLC: Rf=0.6 (cyclohexane/AcOEt 8/2 v/v)

$^1$H NMR (400 MHz; CDCl$_3$) δ=7.32-7.13 (m, 8H$_{2,3,5,6,8,9,11,12}$), 5.81 (s, 1H$_i$), 3.89 (dt, 2H$_b$, J=10.6, 7.2), 2.86 (dt, 2H$_a$, J=10.6, 7.2), 2.59 (t, 2H$_j$, J=7.8), 1.59 (m, 2H$_k$), 1.30 (m, 14H$_{l+m}$), 1.05 (m, 21H$_{c+d}$), 0.89 (t, 3H$_n$, J=6.7)

$^{13}$C NMR (50 MHz; CDCl$_3$) δ=142.9, 142.5 (C$_{7+4}$ for the 2 peaks), 141.9 (C$_{10}$), 139.2 (C$_i$), 129.9, 129.1, 127.1 (C$_{2,3,5,6,8,9,11,12}$ for the 3 peaks), 76.7 (C$_i$), 65.5 (C$_b$), 40.1 (C$_a$), 36.3 (C$_j$), 32.6, 32.2, 30.3, 30.2, 30.0 (C$_{k,l}$ for the 5 peaks), 23.4 (C$_m$), 18.6 (C$_d$), 14.8 (C$_n$), 12.7 (C$_c$)

Mass: m/z=547.4 [M+Na]$^+$, calculated mass=524.4 g·mol$^{-1}$

Synthesis of 2-(4-((4-decylphenyl)(hydroxy)methyl)phenyl)ethanol (8)

$C_{25}H_{36}O_2$—MW: 368.5 g·mol$^{-1}$

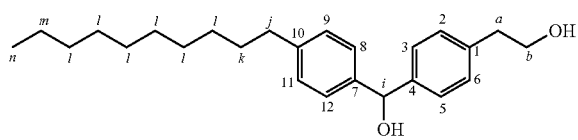

7b (842 mg-1.60 mmol) is dissolved in 10 mL of THF under stirring and tetra-n-butylammonium fluoride (3 mL-3 mmol) is added to the solution. The latter is left under stirring for 1.5 hour. 10 mL of a saturated NaHCO$_3$ solution are added to the solution and the latter is then extracted with AcOEt. The recovered organic phases are washed with a solution of saturated NaHCO$_3$ solution and then dried on MgSO$_4$, filtered and the solvent is evaporated under reduced pressure. The resulting residue is purified on silica gel (elution gradient CH$_2$Cl$_2$/MeOH 100/0 to 98/2 v/v) in order to lead to the product 8 obtained in the form of a white solid (427 mg—Yield: 73%)

TLC: Rf=0.5 (CH$_2$Cl$_2$/MeOH 9/1 v/v)

$^1$H NMR (300 MHz; CDCl$_3$) δ=7.36-7.14 (m, 8H$_{2,3,5,6,8,9,11,12}$), 5.82 (s, 1H$_i$), 3.85 (m, 2H$_b$), 2.86 (t, 2H$_a$, J=6.5), 2.58 (t, 2H$_j$, J=7.8), 1.59 (m, 2H$_k$), 1.26 (m, 14H$_{l+m}$), 0.89 (t, 3H$_n$, J=6.7)

$^{13}$C NMR (50 MHz; CDCl$_3$) δ=143.0 (C$_7$), 142.9 (C$_4$), 141.8 (C$_{10}$), 138.3 (C$_1$), 129.7 (C$_{9,11}$), 129.2 (C$_{2,6}$), 127.4 (C$_{8,12}$), 127.1 (C$_{3,5}$), 76.6 (C$_i$), 64.2 (C$_b$), 39.5 (C$_a$), 36.3 (C$_j$), 32.6, 32.1, 30.3, 30.2, 30.0 (C$_{k+l}$ for the 5 peaks), 23.4 (C$_m$), 14.8 (C$_n$)

Mass: m/z=351.2 [M+H—H$_2$O]$^+$, calculated mass=368.3 g·mol$^{-1}$ (4-(4-decylbenzoyl)phenyl)ethanoic acid (1c)

$C_{25}H_{32}O_3$—MW: 380.5 g·mol$^{-1}$

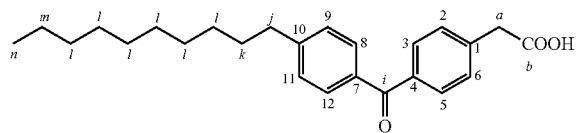

8 (410 mg-1.11 mmol) is dissolved in 10 mL of acetone and then 1 mL of Jones reagent 2.67 M (26.72 g of chromium trioxide, 23 mL of concentrated sulfuric acid, 77 mL of water) is added dropwise to the solution. The latter is stirred at room temperature for 2 hours. The excess of reagent is reduced by a few drops of isopropanol. 20 mL of water are then added to the reaction medium in order to dissolve the chromium salt precipitate. The acetone is evaporated under reduced pressure. The aqueous phase is then extracted with CH$_2$Cl$_2$ (4×20 mL). The recovered organic phases are dried on MgSO$_4$, filtered and the solvent is evaporated under reduced pressure. The resulting residue is purified on a silica column (elution gradient cyclohexane/AcOEt 95/5 to 85/15 v/v) in order to lead to the product 1c obtained in the form of a white solid (384 mg—Yield: 91%)

TLC: Rf=0.4 (CH$_2$Cl$_2$/MeOH 9/1 v/v)

Melting point: 71.0-72.5° C.

$^1$H NMR (300 MHz; CDCl$_3$) δ=7.77 (dd, 4H$_{3,5,8,12}$, J=12.8, 8.2), 7.35 (dd, 4H$_{2,6,9,11}$, J=38.7, 8.1), 3.76 (s, 2H$_a$), 2.69 (t, 2H$_j$, J=7.7), 1.64 (m, 2H$_k$), 1.28 (m, 14H$_{l+m}$), 0.89 (t, 3H$_n$, J=6.4)

$^{13}$C NMR (50 MHz; CDCl$_3$) δ=196.8 (C$_i$), 177.4 (C$_b$), 149.0 (C$_{10}$), 138.3, 137.6, 135.6 (C$_{1,4,7}$ for the 3 peaks), 131.0, 130.0, 129.0 (C$_{2,3,5,6,8,9,11,12}$ for the 3 peaks), 41.6 (C$_a$), 36.7 (C$_j$), 32.6, 31.8, 30.2, 30.0 (C$_{k+l}$ for the 4 peaks), 23.3 (C$_m$), 14.8 (C$_n$)

Mass: m/z=381.2 [M+H]$^+$, calculated mass=380.2 g·mol$^{-1}$

Rhod-Dpr(FABP)-NH—C$_{16}$H$_{33}$

Boc-L-Dpr(FABP)-OH (9)

To a solution of FABP (1 equiv.) in anhydrous dichloromethane, are added DIEA (5 equiv.) and PyBOP (1 equiv.). The solution is stirred for 10 mins before activating the acid. Then, Boc-L-Dpr-OH (1 equiv.) solubilized in a mixture of anhydrous dichloromethane and methanol (3/2 v/v) is added to the previous solution. The resulting solution is stirred at room temperature, away from light. Then, the organic phase is washed with a saturated NaHCO$_3$ solution and the aqueous phase is extracted with CH$_2$Cl$_2$. The recovered organic phases are dried on MgSO$_4$, filtered and the solvent is evaporated under reduced pressure. The resulting residue is purified on a silica column (elution gradient CH$_2$Cl$_2$/MeOH 100/0 to 100/15 v/v).

Example with (S)-2-(tert-butoxycarbonylamino)-3-(6-(4-(4-hexylbenzoyl)phenyl)hexanamido) propanoïc acid (9a)

Reaction time: 12 h; TLC: Rf=0.3 (CH$_2$Cl$_2$/MeOH v/v 9/1); $^1$H NMR (300 MHz; CDCl$_3$) δ=7.67 (m, 4H), 7.24 (m, 4H), 4.14 (m, 1H), 3.73 (q, 1H, J=7.0), 3.14 (q, 1H, J=7.0), 2.65 (m, 4H), 2.17 (m, 2H), 1.62-1.21 (m, 23H), 0.87 (m, 3H). Mass: m/z=567.4 [M+H]$^+$, calculated mass=566.3 g·mol$^{-1}$ Boc-L-Dpr(FABP)-NH—C$_{16}$H$_{33}$ (10)

To a solution of Boc-L-Dpr(FABP)-OH (1 equiv.) in anhydrous dichloromethane, DIEA (5 equiv.) and PyBOP (1.3 equiv.) are added and this solution is stirred for 10 mins in order to activate the acid. Then, hexadecylamine (1 equiv.) is added to the solution which is stirred at room temperature, away from light. Then, the organic phase is washed with a saturated NaHCO$_3$ solution and the aqueous phase is extracted with CH$_2$Cl$_2$. The recovered organic phases are dried on MgSO$_4$, filtered and the solvent is evaporated under reduced pressure. The resulting residue is purified on a silica column (elution gradient CH$_2$Cl$_2$/MeOH 100/0 to 100/4 v/v).

Example with (S)-tert-butyl 1-(hexadecylamino)-3-(6-(4-(4-hexylbenzoyl)phenyl)hexanamido)-1-oxo-propan-2-ylcarbamate (10a)

Reaction time: 6 hours; TLC: Rf=0.4 (CH$_2$Cl$_2$/MeOH 9/2 v/v); $^1$H NMR (300 MHz; CDCl$_3$) δ=7.73 (m, 4H), 7.27 (m, 4H), 6.86 (s, 1H), 6.35 (s, 1H), 5.98 (d, 1H, J=6.0), 4.16 (m, 1H), 3.71 (m, 1H), 3.51 (m, 1H), 3.23 (m, 2H), 2.69 (t, 4H, J=7.5), 2.20 (t, 2H, J=7.5), 1.70-1.25 (m, 51H), 0.88 (m, 6H); $^{13}$C NMR (75 MHz; CDCl$_3$) δ=196.9, 175.5, 171.1, 148.6, 148.0, 136.3, 136.0, 130.9, 128.9, 81.0, 42.7, 40.2, 37.0, 36.7, 36.4, 32.6, 32.4, 31.8, 31.5, 30.4-29.5, 29.0, 27.5, 26.1, 23.3, 14.7. Mass: m/z=790.7 [M+H]$^+$, calculated mass=789.6 g·mol$^{-1}$ H-L-Dpr(FABP)-NH—C$_{16}$H$_{33}$ (11)

Boc-L-Dpr(FABP)-NH—C$_{16}$H$_{33}$ is dissolved in a 1/1 v/v CH$_2$Cl$_2$/TFA 1/1 v/v solution. This solution is stirred for 1 hour at room temperature away from light and then diluted with CH$_2$Cl$_2$. The organic phase is washed with a saturated NaHCO$_3$ solution and the aqueous phase is extracted with CH$_2$Cl$_2$. The recovered organic phases are dried on MgSO$_4$, filtered and the solvent is evaporated under reduced pressure.

Example with (S)—N-(2-amino-3-(hexadecylamino)-3-oxopropyl)-6-(4-(4-hexylbenzoyl)phenyl)hexanamide (11a)

Reaction time: 1 h; TLC: Rf=0.4 ($CH_2Cl_2$/MeOH 9/1 v/v); $^1H$ NMR (300 MHz; $CDCl_3$) δ=7.73 (m, 4H), 7.50 (m, 1H), 7.27 (m, 4H), 6.29 (m, 1H), 3.65 (m, 1H), 3.47-3.37 (m, 2H), 3.23 (m, 2H), 2.69 (t, 4H, J=7.5), 2.20 (t, 2H, J=7.5), 1.66-1.25 (m, 42H), 0.88 (m, 6H); $^{13}C$ NMR (75 MHz; $CDCl_3$) δ=196.9, 174.8, 173.9, 148.6, 148.0, 136.2, 136.0, 130.8, 128.9, 55.9, 44.3, 39.8, 37.2, 36.6, 36.4, 32.6, 32.3, 31.8, 31.4, 30.3-29.5, 27.6, 26.1, 23.3, 14.7. Mass: m/z=690.5 $[M+H]^+$, calculated mass=689.5 $g \cdot mol^{-1}$ Rhod-Dpr(FABP)-NH—$C_{16}H_{33}$ (12)

To a solution of CTMR (1.3 equiv.) in anhydrous dichloromethane, DIEA (5 equiv.) and PyBOP (1.3 equiv) are added and this solution is stirred for 10 mins in order to activate the acid. Then, H-L-Dpr(FABP)-NH—$C_{16}H_{33}$ (1 equiv.) solubilized in anhydrous dichloromethane is added to the previous solution. The resulting solution is stirred at room temperature, away from light. Then, the solvent is evaporated under reduced pressure. The resulting residue is purified on a silica column (elution gradient $CH_2Cl_2$/MeOH 100/0 to 100/15 v/v).

Example with Rhod-Dpr(CO—C—BP—$C_6$)—NH—$C_{16}H_{33}$ (12a)

Reaction time: 24 h; TLC: Rf=[0.7; 0.5]($CH_2Cl_2$/MeOH 9/2 v/v); HRMS calculated for $C_{69}H_{92}N_5O_7$=1102.6997 found 1102.6961; HPLC: Rt=13.6 min Example of an Identification Method Reagents:
Dodecylphosphocholine (DPC) and *Halobacterium salinarum* bacterio-rhodopsin are from SIGMA. Egg yolk phosphatidylcholine (PC) and cholesterol (chol, 99% pure) are from Avanti Polar Lipids (Alabaster, USA).

Preparation of the Liposomes:
PC, chol and the lipid tool (12a-c) (molar ratio 65:30:5) dissolved in chloroform are mixed in a test tube. After evaporation of the solvent with heat (45 mins at 37° C.), the dry film is hydrated by adding 300 μl of PBS at pH 7.4 in order to obtain a final concentration of lipids of 5 mM. The mixture is stirred and the resulting suspension is heated to 37° C., and then cooled in liquid nitrogen 5 times, and then passed through an extruder equipped with two 100 nm filters (35 passages).

Fluorescence Spectroscopy:
The excitation and emission spectra of the probe compounds according to the invention, within liposomes are recorded at 32° C. on a TECAN Infinite M1000 spectrofluorimeter. The lipid composition of the liposomes is PC:chol:lipid-tool 65:30:5 (molar ratio). The <<blank>> control liposomes consist of PC:chol, and their residual fluorescence is subtracted from the measured fluorescence spectra.

Photomarking of Bacteriorhodopsin:
DPC is added to a compound as a solution in chloroform-methanol (2/1, v/v) in the compound/detergent proportion of 1:50 molar. After evaporation in a high vacuum for 2 hours, the dry lipid film is hydrated by adding 50 μL of distilled water and 50 μl of Tris-HCl pH 8.0. The bacteriorhodopsin resuspended in distilled water, is incubated with the compounds according to invention in detergent micelles, in a protein-compound molar ratio of 1:5. The mixture is then left for 1 hour in darkness at 4° C., and then subject for 45 s to UV irradiation with a UV Flood Dymax device, equipped with a high pressure mercury lamp 400 W, placed at a distance of 10 cm from the sample in a quartz bowl. Laemmli buffer is then added to the irradiated mixture and then incubated for 15 mins at room temperature. Analysis is conducted on an electrophoresis gel (15% of acrylamide/20% of glycerol). After migration, the gel is first analyzed on a Fluorimager Typhoon 8600 equipped with a rhodamine filter, in order to detect fluorescence; the gel is then colored with Coomassie blue for viewing all the protein bands.

It is then seen that the protein is only viewed with the Fluorimager after photomarking and that it is not degraded under the conditions of our test (Coomassie coloring). Further, the efficiency of the covalent bridging depends on the distance between the double aromatic ring of benzophenone and the carbonyl (cf. Table 1).

TABLE 1

| Name | Chemical formula | d (Å) | Intensity of the photomarking signal (arbitrary units - AU) |
|---|---|---|---|
| $C_1$-BP-$C_{10}$-COOH distal FABP (1b) | | 18.7 | 10 |
| $C_6$-BP-$C_5$-COOH medium FABP (1a) | | 12.7 | 5 |

TABLE 1-continued

| Name | Chemical formula | d (Å) | Intensity of the photomarking signal (arbitrary units - AU) |
|---|---|---|---|
| $C_{10}$-BP-$C_1$-COOH proximal FABP (1c) | | 7.9 | 1 |

The invention claimed is:

1. A compound consisting of a trifunctional binding platform substituted with:
  at least one chromophore group selected from an absorbing group, a fluorescent group or a luminescent group;
  a first functionalized hydrocarbon chain, the chain being functionalized at an end that links the chain to the platform; and
  a second functionalized hydrocarbon chain, comprising a photoreactive group, the chain being functionalized at an end that links the chain to the platform.

2. The compound according to claim 1, wherein the compound is hydrophobic.

3. A compound having the formula (I), comprising a trifunctional binding platform Q, substituted with:
  at least one chromophore group Q1 selected from an absorbing group, a fluorescent group or a luminescent group;
  a first hydrocarbon chain bound to Q via a functional group L1; and
  a second hydrocarbon chain bound to Q via a functional group L2 and comprising a photoreactive group Q2,

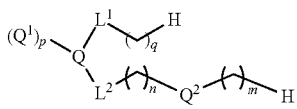

(I)

wherein
  Q represents the trifunctional binding platform;
  p represents 1, 2 or 3;
  Q1, either identical or different, independently represents a chromophore group selected from an absorbing group, a fluorescent group or a luminescent group;
  L1 and L2, either identical or different, independently represent a group selected from NH, C(O), S, and O;
  Q2 represents a photoreactive group;
  m represents an integer from 0 to 24;
  n represents an integer from 1 to 24;
  the sum of m and of n is between 1 and 30; and
  q represents an integer from 1 to 30.

4. The compound according to claim 3, wherein
  when p represents 1 then Q1 represents a fluorescent group;
  when p represents 2 then Q1 represents two identical or different fluorescent groups; a fluorescent group and an absorbing group; or a fluorescent group and a luminescent group; and
  when p represents 3 then Q1 represents a luminescent group and two identical or different fluorescent groups.

5. The compound according to claim 4, wherein the trifunctional binding platform comprises a group selected from amino acid derivatives, glycerol derivatives, carboxylic tri-acid derivatives, and triamine derivatives.

6. The compound according to claim 5, wherein the trifunctional binding platform comprises a group derived from an alpha-amino acid and comprising two amine functions and a carbonyl function.

7. The compound according to claim 6, having the formula (II),

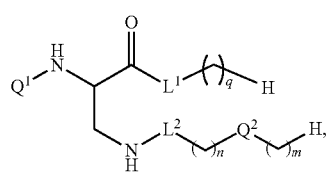

(II)

wherein $Q^1$, $L^1$, $L^2$, $Q^2$, m, n and q are as previously defined.

8. The compound according to claim 7, having the formula (III),

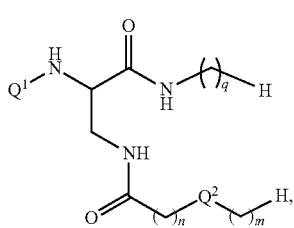

(III)

wherein $Q^1$, $Q^2$, m, n and q are as previously defined.

9. The compound according to claim 1, wherein the chromophore group is independently selected from rhodamine, fluorescein, rhodamine derivatives, substituted rhodamine, fluorescein derivatives, substituted fluorescein, coloring agents, colored substances absorbing in the visible (400 to 800 nm), luciferin, luminol, and luminol derivatives.

10. The compound according to claim 9, wherein the chromophore group is selected from rhodamine and its analogs.

11. The compound according to claim 10, wherein the chromophore group is carboxytetramethylrhodamine.

12. The compound according to claim 3, wherein
  m represents an integer from 1 to 12; or
  n represents an integer from 1 to 12, or
  q represents an integer from 6 to 26; or
  the sum of m and of n is between 4 and 24.

13. The compound according to claim 12 wherein
m represents an integer from 1 to 12; and
n represents an integer from 1 to 12; and
q represents an integer from 8 to 24; and
the sum of m and of n is between 6 and 18.

14. The compound according to claim 1, wherein the photoreactive group is independently selected from carbene generating groups, nitrene generating groups, and derivatives of arylketone.

15. The compound according to claim 14, wherein the photoreactive group is independently selected from a group comprising a diazo or diazoester function, a group derived from diazirine, a group comprising an arylazide, acylazide, alkylazide, diazoester function, a group derived from benzophenone, and a group of formula (IV)

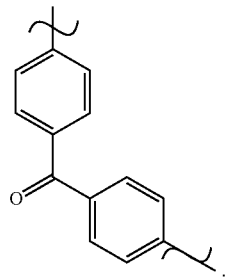

(IV)

16. A method for preparing a compound according to claim 1 by reacting
a compound comprising an trifunctional binding platform;
at least one compound comprising a chromophore group selected from an absorbing group, a fluorescent group and a luminescent group;
a compound comprising a first hydrocarbon chain and functionalized at one end; and
a compound comprising a second hydrocarbon chain, functionalized at one end and comprising a photoreactive group.

17. The method according to claim 16, for which the compound comprising the trifunctional binding platform comprises a free primary amine function, a protected primary amine function, and a carboxylic acid function.

18. The method according to claim 17, comprising
reacting the free primary amine function with the compound comprising a first hydrocarbon chain functionalized at one end;
reacting the carboxylic acid function with the compound comprising a second hydrocarbon chain, functionalized at one end and comprising a photoreactive group;
deprotecting the protected primary amine function; and
reacting the deprotected primary amine function with the compound comprising a chromophore group selected from an absorbing group, a fluorescent group or a luminescent group.

19. A method for identifying a protein comprising utilizing the compound according to claim 1.

20. The method according to claim 19, comprising identifying a hydrophobic fragment within a protein.

21. The method according to claim 19, comprising identifying one or more transmembrane domains within a membrane protein.

22. The method according to claim 19, comprising identifying a fusion protein.

23. The method according to claim 19 comprising identifying a viral fusion peptide.

24. The method according to claim 19, comprising identifying a fusion protein of a hepatitis virus, of HIV, of an influenza virus, or of a veterinary virus.

25. The method according to claim 24, comprising identifying a fusion protein of a virus of hepatitis B or hepatitis C.

26. The method according to claim 19, comprising
a—contacting the compound with the protein;
b—photoactivating the compound or the photoreactive group of the compound;
c—reacting the photoactivated group of the compound with the protein; and
d—activating and detecting or detecting fluorescence or absorbance of the chromophore group within the reaction product.

27. The method according to claim 26, wherein the contacting of the compound with the protein is carried out by means of micelles or systems with lipid bilayers.

28. The method according to claim 27, wherein the lipid bilayer systems are liposomes.

29. The method according to claim 26, wherein photoactivation is achieved
with a source selected from a lamp or a laser; or
the activation power is between 0.1 and 1,000 W; or
the wavelength is between 250 and 500 nm; or
the activation time is between 1 second and 2 hours.

* * * * *